(12) United States Patent
Coon

(10) Patent No.: US 8,493,224 B2
(45) Date of Patent: Jul. 23, 2013

(54) BOWDEN CABLE WEAR DETECTION IN A TUBE CLAMP SYSTEM FOR MEDICAL FLUIDS

(75) Inventor: Zachary A. Coon, Plymouth, MI (US)

(73) Assignee: Terumo Cardiovascular Systems Corp., Ann Arbor, MI (US)

( * ) Notice: Subject to any disclaimer, the term of this patent is extended or adjusted under 35 U.S.C. 154(b) by 319 days.

(21) Appl. No.: 13/041,919

(22) Filed: Mar. 7, 2011

(65) Prior Publication Data

US 2012/0229289 A1    Sep. 13, 2012

(51) Int. Cl.
*G08B 21/00* (2006.01)
(52) U.S. Cl.
USPC ............... 340/652; 340/635; 604/65; 604/67
(58) Field of Classification Search
None
See application file for complete search history.

(56) References Cited

U.S. PATENT DOCUMENTS

| | | | |
|---|---|---|---|
| 4,818,177 A | | 4/1989 | Grohmann |
| 5,445,613 A | * | 8/1995 | Orth ................................ 604/66 |
| 6,386,505 B2 | | 5/2002 | Schöb |
| 7,157,920 B2 | | 1/2007 | Barber et al. |
| 7,367,540 B2 | | 5/2008 | Brieske |
| 2008/0071291 A1 | * | 3/2008 | Duval et al. ................... 606/130 |
| 2013/0053868 A1 | * | 2/2013 | Cooper et al. ................. 606/130 |

* cited by examiner

*Primary Examiner* — Julie Lieu
(74) *Attorney, Agent, or Firm* — Gael Diane Tisack, Esq.; Darryl Newell; McMillan, Sobanski & Todd

(57) ABSTRACT

A system for clamping a flexible tube containing medical fluids includes a cable assembly coupled to a remote driver and a slidable clamp that imparts a clamping force to the flexible tube. An electrical continuity detector is included to measure the wear of an internal insulating layer of the cable between a sliding inner wire and a cable casing member. An indication of the wear to the cable is generated in response to a comparison of the electrical integrity of the insulating layer with a threshold. The wear indication enables the cable to be repaired or replaced prior to a malfunction of the overall tube clamp system.

8 Claims, 2 Drawing Sheets

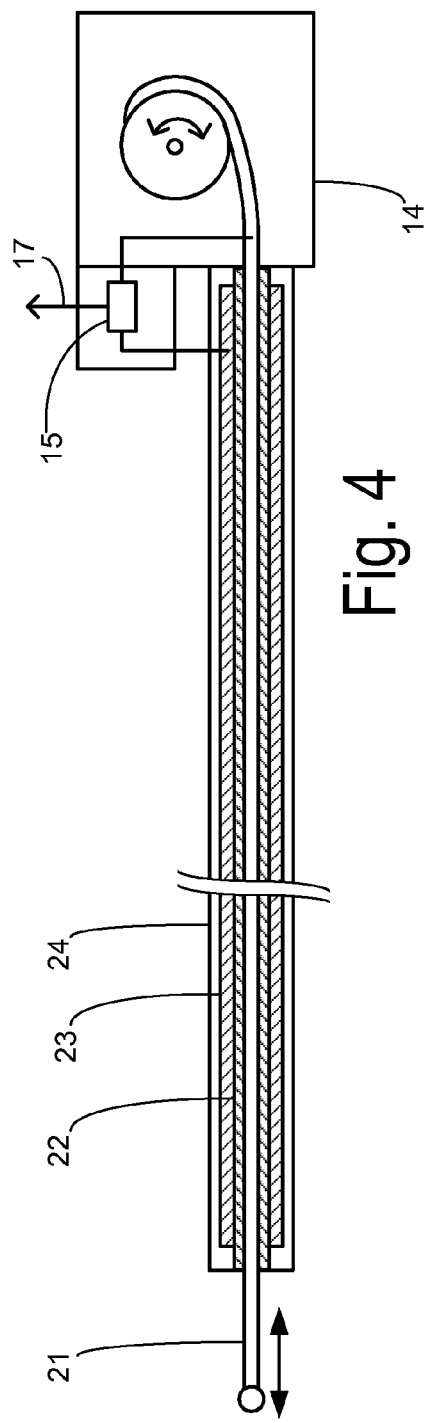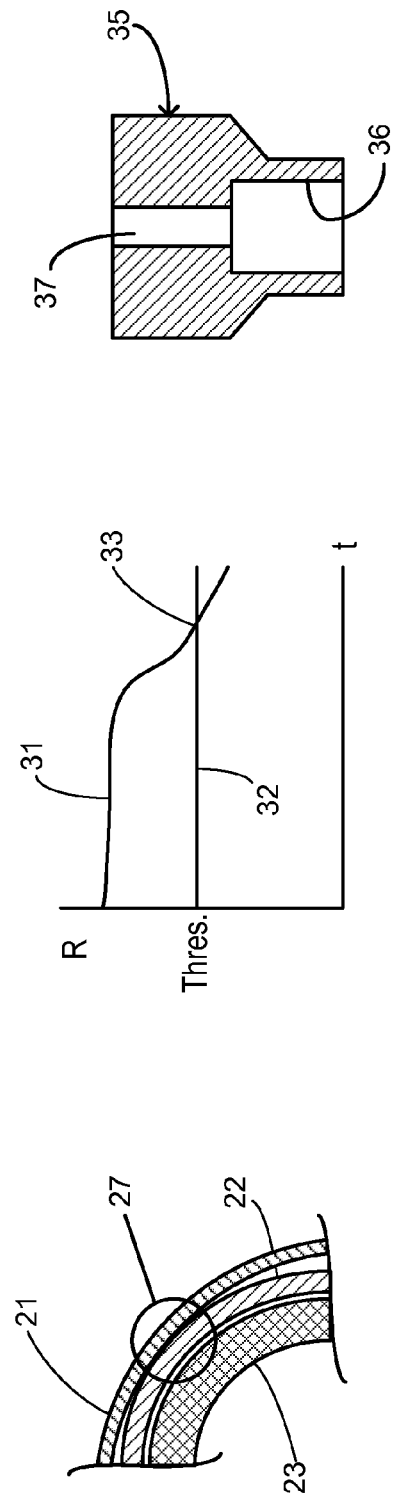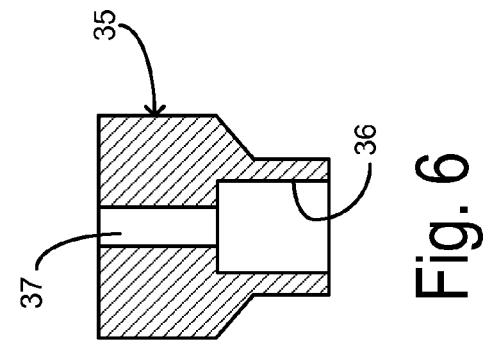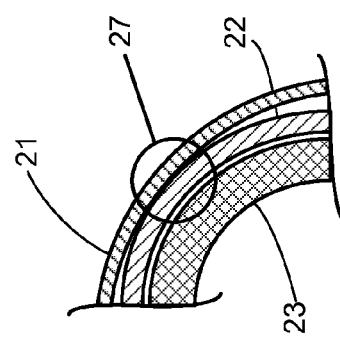

BOWDEN CABLE WEAR DETECTION IN A TUBE CLAMP SYSTEM FOR MEDICAL FLUIDS

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to a system and method for monitoring the proper operational condition of a Bowden cable, and more particularly to detecting friction-induced wear within a Bowden cable used in a system for clamping a tube containing medical fluids, thereby enabling maintenance or replacement of the cable prior to failure.

Many medical procedures involve transporting fluids such as blood or medicinal solutions within flexible tubing. Is it often necessary for the safety and efficacy of the medical procedure to control the flow rate of the fluids being transported. One common means of controlling the flow rate is to occlude the tubing by applying a compressive clamping force to it, thereby constricting the passage of the fluid within the tube.

Various systems have been used to control the flow rate of medical fluids by applying a compressive clamping force to flexible tubing. Typical clamping systems have used a solenoid-driven piston to pinch the tubing against a plate. Such systems have been relatively heavy, resulting in the need for mounting supports for the clamp.

A newly improved clamping system including a flexible cable assembly component commonly referred to as a Bowden cable for transmitting a mechanical clamping force from a remote driver to an actuator which is in contact with the tubing is described in copending application U.S. serial number (17916), entitled "Light Weight Tube Clamp for Medical Fluids," filed contemporaneously herewith. This application is hereby incorporated by reference in its entirety.

Bowden cables comprise a flexible hollow outer casing containing a slidable inner wire or wire rope. Bowden cables are well known for their use in conjunction with bicycle brakes. By mechanically anchoring the outer casing and permitting the inner wire to slide within the outer casing, the Bowden cable can transmit longitudinal pulling or pushing forces from one end of the inner wire to the other.

The cylindrical outer casing of a Bowden cable includes a coiled metal wire or rod to provide longitudinal stiffness together with the ability to easily bend the Bowden cable along a desired path. To minimize the amount of force required to operate the Bowden cable, it is desirable to minimize the friction acting upon the inner wire as it slides within the casing. Since the inner wire is also usually made of metal, the resistance would be relatively high if it directly contacted the coiled metal wire of the casing. To that end, Bowden cables typically include a friction-reducing material layer disposed between the outer casing and inner wire, usually in the form of a cylindrical plastic liner.

Over long periods of use, the friction-reducing material layer in a Bowden cable is prone to eventually wear out. It can also be damaged through kinking of the Bowden cable. Any break in the layer can result in loss of its ability to reduce the friction. When that happens, the driving system (such as a motor) of the Bowden cable may be inadequate to function effectively, and the system in which it is installed may become inoperable.

A malfunction of a Bowden cable employed in a medical device, such as a tube clamp system for medical fluids, is particularly critical. Therefore, a means for monitoring the physical integrity and performance of the friction reducing material layer in a Bowden cable used in a tube clamp system for medical fluids, thereby enabling maintenance or replacement of the cable prior to failure, is highly desirable.

SUMMARY OF THE INVENTION

The present invention provides a system for controlling the flow rate of medical fluids. The system includes a means for monitoring the integrity of one of its elements that is susceptible to wear, thereby allowing preventive maintenance of the system prior to malfunction.

In one aspect of the invention, a system for clamping a tube containing medical fluids is provided. An axially movable inner wire is coupled at one end to a slidable clamp and at the other end to a driver, wherein the inner wire is an electrical conductor. An elongated hollow outer casing is provided, wherein the inner wire is coaxially and slidably disposed substantially within the casing, and wherein the casing is comprised of an electrically conductive cylindrical member. An insulating layer is disposed between the inner wire and the electrically conductive cylindrical member. The insulating layer electrically isolates the inner wire from the electrically conductive cylindrical member, and the insulating layer is subject to wear as the inner wire slides within the casing. An electrical continuity detector is coupled to the inner wire and the electrically conductive cylindrical member, wherein the detector is configured to compare the continuity between the inner wire and the electrically conductive cylindrical member with a threshold, and to generate a wear indication in response to the comparison.

BRIEF DESCRIPTION OF THE DRAWINGS

FIG. 3 is a partial cross-sectional view of a wear point within the Bowden cable.

FIG. 4 is a schematic partial section view showing an electrical continuity detector in relation to other elements of a tube clamp system.

FIG. 5 is a graph illustrating the effects of use-based mechanical wear on the electrical continuity of the insulating layer within a Bowden cable.

FIG. 6 is a cross section of an adapter for terminating the Bowden cable.

DETAILED DESCRIPTION OF PREFERRED EMBODIMENTS

In the present invention, a tube clamp is remotely actuated by a driver via a Bowden cable. In addition, an electrical continuity detector monitors an insulating layer within the Bowden cable to provide an indication of wearing of the layer.

Figure 1:
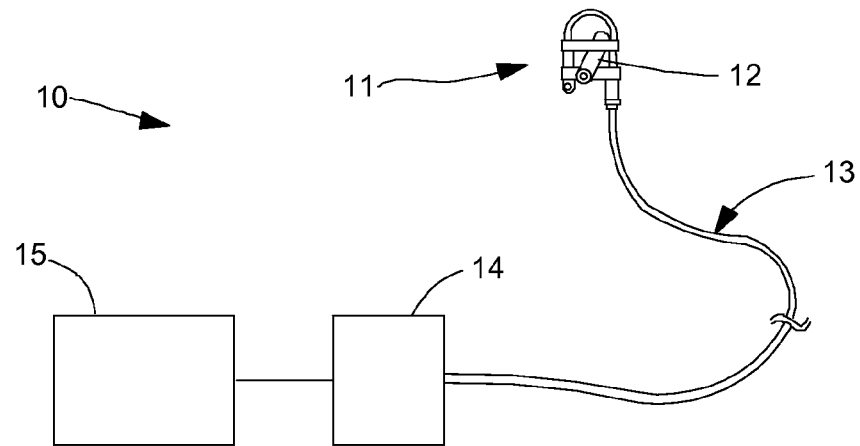
FIG. 1 is a schematic view of a tube clamp system according to one embodiment of the invention.

FIG. 1 illustrates a system 10 for controlling the flow rate of medical fluids transported in flexible tubing. System 10 broadly includes a slidable clamp 11, a flexible tube 12, a Bowden cable 13, a driver 14, and an electrical continuity detector 15. Bowden cable 13 is coupled on one end to actuator 11 and on its other end to driver 14. Mechanical pushing or pulling forces are generated by driver 14 and transmitted by Bowden cable 13 to slidable clamp 11. Slidable clamp 11 applies a variable compressive force on tube 12. The compressive force applied to tube 12 deflects tube 12 to create an occlusion which constricts or fully blocks the flow of medical fluids in tube 12. Electrical continuity detector 15 is in electrical communication with elements of Bowden cable 13 in order to provide a wear status indication of Bowden cable 13 as described below.

Figure 2:
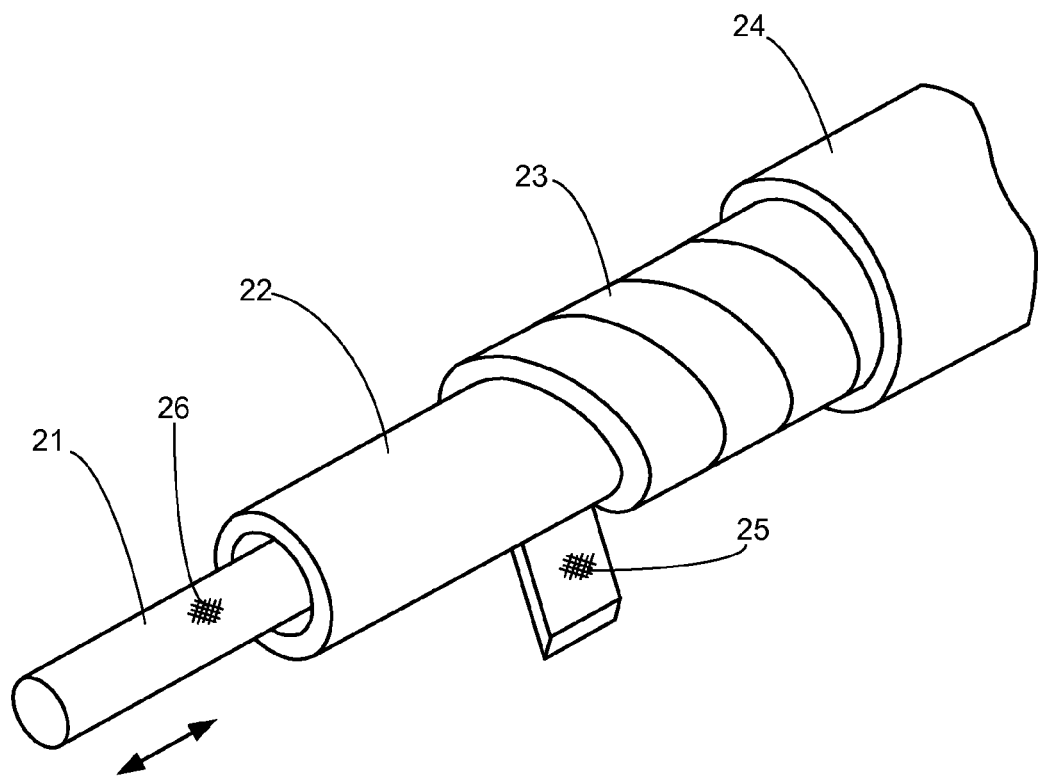
FIG. 2 is a perspective cutaway view illustrating elements of the Bowden cable.

FIG. 2 is shown as a cutaway to illustrate the internal elements of Bowden cable 13. An inner wire 21 may be comprised of a single solid body or may include a plurality of twisted strands to form a wire rope. The solid body or strands are made of a conductive metal such as steel. One or both ends of inner wire 21 may include a nipple (not shown) for attaching to other components. Inner wire 21 is coaxially disposed within an outer casing that includes a spiral wound casing member 23 and a protective housing 24. Member 23 is made to be substantially incompressible in an axial direction but flexible in a lateral direction. One of ordinary skill in the art will recognize casing member 23 can be constructed in various ways. Instead of the rectangular wire shown in FIG. 2, a steel wire with a round or other cross section can be used. Instead of a single spiral, the coiled casing member 23 could include multiple spiral strands woven together. A seamless tubular metal material could also be used.

Between inner wire 21 and casing member 23 is an insulating layer in the form of a cylindrical plastic sheath 22. In operation, casing member 23 is rigidly secured on each of its ends, while inner wire 21 is freely slidable along its longitudinal axis with respect to the outer casing. The axial movement of inner wire 21 in relation to casing member 23 enables Bowden cable 13 to transmit mechanical pushing and pulling forces.

Insulating layer 22 is disposed between inner wire 21 and outer casing 23 for the purpose of reducing friction, but it also acts as an insulating barrier between inner wire 21 and outer wire 23. Insulating layer 22 is made from a material that is not electrically conductive such as vinyl or other polymeric material. Rather than a separate tubular sheath as shown in FIG. 2, layer 22 may alternatively be comprised of a coated layer of insulating material applied to either the inner surface of casing member 23 as shown at 25 or the outer surface of inner wire 21 as shown at 26.

FIG. 3 illustrates the concentration of wear in an area 27 where the Bowden cable bends. Along the inner radius of a bend, inner wire 21 has its most forceful contact with sheath 22. As sheath 22 becomes worn away, increasing exposure of inner wire 21 to casing member 23 results. Sliding friction of inner wire 21 goes up while electrical continuity between inner wire 21 and casing member 23 goes up (i.e., electrical resistance goes down).

FIG. 4 shows the wear detection of the invention in greater detail. Inner wire 21 of Bowden cable 13 is coupled to driver 14. Driver 14 may use various mechanisms for applying motive force to inner wire 21 such as a rotary spindle coupled to a stepper motor, a linear motor, a double acting fluid mechanical cylinder and so on. Since insulating layer 22 electrically isolates inner wire 21 and casing member 23, the physical integrity of insulating layer 22 can be detected by examining the electrical continuity between inner wire 21 and casing member 23 as measured by electrical continuity detector 15. Detector 15 is electrically connected to casing member 23 and inner wire 21 in any suitable manner. Since inner wire 21 is movable, it is preferable to make a fixed connection to a portion of inner wire 21 that is inside the housing of driver 14 where there is no interference with its movement into the outer casing. The connection to casing member 23 may preferably be made by a standalone connection just outside the housing of driver 14. Detector 15 measures an electrical property between inner wire 21 and casing member 23, and when the measured property corresponds to a continuity greater than a threshold (e.g., a resistance in ohms less that a predetermined resistance), then a warning signal 17 is generated. The electrical continuity between the inner wire and the casing member can be measured according to electrical properties other than resistance, such as capacitance or inductance. Warning signal 17 may be in the form of the turning on of a warning light or may be a communicated signal that is sent to an electronic control system, for example.

FIG. 5 illustrates the monitoring and eventual decline of the physical integrity of the insulating layer of a Bowden cable as a function of time. The y-axis of the graph in FIG. 5 is a scale of electrical continuity. The x-axis is time, such as hours of operation of a Bowden cable. The electrical continuity detector of the present invention measures the continuity of the insulating layer and compares it to a threshold level. The measured continuity of the insulating layer as a function of time is represented by line 31 in FIG. 5. Line 32 represents a threshold level of continuity which is established to correspond to the level of continuity at which the insulating layer has failed or is close to failure. The threshold level may be determined empirically by experimentation. In an undamaged Bowden cable the electrical resistance of the insulating layer is high, as shown by line 41 at "t=0" on the left side of the graph in FIG. 5. With use, the friction from the sliding of the Bowden cable's inner wire will induce wearing of the insulating layer so that its thickness decreases at one or more places. The resistance of the thinning insulating layer is reduced as shown by the decline in line 31 going from left to right on the graph. At a point 33, the resistivity of the insulating layer has declined to the extent that it is equal to the threshold value represented by line 32. Point 33 represents the decline in the physical integrity of the insulating layer to the extent that the Bowden cable should be repaired or replaced.

FIG. 6 illustrates an adapter 35 for connecting a Bowden cable with devices at its terminations, such as a driver housing. A socket 36 receives an end of the outer casing. Socket 36 and the outer casing may be threaded in order to attach them by screwing them together. Crimping or adhesives could also be used. Adapter 35 is formed of an insulating material, such as a plastic, in order to maintain the electrical isolation of the inner wire from the outer casing member.

A passage 37 receives the inner wire which then passes into the device, such as the driver, where it is attached to one of the moving structures in the system. In order to adjust the effective length of the outer casing and thereby the tension or travel path of the inner wire, a barrel adjuster (not shown) or other adjustable feature may be incorporated into adapter 35 or placed at some other location, provided it maintains the electrical isolation between the inner wire and the casing member.

While the invention has been described in reference to a preferred embodiment of a medical fluid tube clamp remotely actuated by a driver via a Bowden cable with an electrical continuity detector to monitor the integrity of an insulating layer within the Bowden cable, it should be understood by those skilled in the art that the essence of the invention may also be applied to other medical and non-medical devices. In addition, various changes may be made and equivalents may be substituted for elements thereof without departing from the essential scope of the invention. Therefore, it is intended that the invention not be limited to the particular embodiment disclosed herein, but that the invention will include all embodiments falling within the scope of the claims.

I claim:

1. A system for clamping a tube containing medical fluids, comprising:
    an axially movable inner wire coupled at one end to a slidable clamp and at the other end to a driver, wherein the inner wire is an electrical conductor;
    an elongated hollow outer casing, wherein the inner wire is coaxially and slidably disposed substantially within the casing, and wherein the casing is comprised of an electrically conductive cylindrical member;
    an insulating layer disposed between the inner wire and the electrically conductive cylindrical member, wherein the insulating layer electrically isolates the inner wire from the electrically conductive cylindrical member, and wherein the insulating layer is subject to wear as the inner wire slides within the casing; and
    an electrical continuity detector coupled to the inner wire and the electrically conductive cylindrical member, wherein the detector is configured to compare the continuity between the inner wire and the electrically conductive cylindrical member with a threshold, and to generate a wear indication in response to the comparison.

2. The system of claim 1, wherein the insulating layer is a tubular liner member.

3. The system of claim 1, wherein the insulating layer is a coating material disposed on the surface of the inner wire.

4. The system of claim 1, wherein the insulating layer is a coating material disposed on the inner surface of the casing.

5. The system of claim 1 wherein the electrically conductive cylindrical member is comprised of a coiled electrical conductor.

6. The system of claim 1, wherein the casing further comprises a tubular housing disposed over the electrically conductive cylindrical member.

7. The system of claim 1, wherein the continuity detector measures resistance.

8. A method for detecting a potential failure of a system for clamping a tube containing medical fluids, the system comprising a Bowden cable assembly with an electrically resistive insulating layer disposed between an electrically conductive inner wire and an electrically conductive outer casing, the method comprising the steps of:
    measuring an electrical continuity between the inner wire and the casing using an electrical continuity detector coupled to the inner wire and the casing; and
    comparing the measured continuity between the inner wire and the casing to a threshold value, wherein the threshold value corresponds to a predetermined reduction in the integrity of the insulating layer; and
    generating a warning indication in response to the comparison.

* * * * *